(12) United States Patent
Klocke et al.

(10) Patent No.: US 10,413,703 B2
(45) Date of Patent: Sep. 17, 2019

(54) CATHETER WITH MARKINGS TO FACILITATE ALIGNMENT

(71) Applicant: CLEARSTREAM TECHNOLOGIES LIMITED, Enniscorthy, County Wexford (IE)

(72) Inventors: Stephanie Klocke, Chandler, AZ (US); Jim C. Beasley, Phoenix, AZ (US); Scott Randall, Mesa, AZ (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 0 days.

(21) Appl. No.: 14/758,609

(22) PCT Filed: Dec. 31, 2013

(86) PCT No.: PCT/IB2013/003054
§ 371 (c)(1),
(2) Date: Jun. 30, 2015

(87) PCT Pub. No.: WO2014/102608
PCT Pub. Date: Jul. 3, 2014

(65) Prior Publication Data
US 2015/0335860 A1    Nov. 26, 2015

Related U.S. Application Data

(60) Provisional application No. 61/747,416, filed on Dec. 31, 2012.

(51) Int. Cl.
*A61M 25/01* (2006.01)
*A61M 25/10* (2013.01)
*A61M 25/00* (2006.01)

(52) U.S. Cl.
CPC .... *A61M 25/0108* (2013.01); *A61M 25/0067* (2013.01); *A61M 25/0105* (2013.01);
(Continued)

(58) Field of Classification Search
CPC ............ A61M 25/0108; A61M 25/104; A61M 2025/0008; A61M 2025/105;
(Continued)

(56) References Cited

U.S. PATENT DOCUMENTS

| | | |
|---|---|---|
| 550,238 A | 11/1895 | Allen, Jr. |
| 4,133,303 A | 1/1979 | Patel |

(Continued)

FOREIGN PATENT DOCUMENTS

| | | |
|---|---|---|
| CA | 2635157 A1 | 12/2009 |
| CN | 201519356 U | 7/2010 |

(Continued)

OTHER PUBLICATIONS www.dictionary.com, dated Oct. 28, 2016, definition for angioplasty, attached as a pdf.*

(Continued)

*Primary Examiner* — Nathan R Price
*Assistant Examiner* — John A Doubrava
(74) *Attorney, Agent, or Firm* — King & Schickli, PLLC

(57) ABSTRACT

For treating a treatment area in the vasculature, this disclosure relates to a first, pre-dilatation catheter having a first shaft including a first distal portion adapted for positioning at the treatment area and a first proximal portion including a first marking at a first location. A second, dilatation catheter includes a second shaft including a second distal portion adapted for positioning at the treatment area and a second proximal portion including a second marking at a second location substantially matching a first location of the first marking. Related methods are disclosed.

10 Claims, 8 Drawing Sheets

(52) U.S. Cl.
CPC ...... *A61M 25/104* (2013.01); *A61M 25/1011* (2013.01); *A61M 2025/006* (2013.01); *A61M 2025/0008* (2013.01); *A61M 2025/105* (2013.01)

(58) Field of Classification Search
CPC .......... A61M 25/0067; A61M 25/0105; A61M 25/1011; A61M 2025/006; A61M 25/01; A61M 25/10; A61M 25/00; A61M 2205/6063; A61B 90/39; A61B 2017/00796; A61B 5/06
USPC .................................. 604/510; 600/424, 117
See application file for complete search history.

(56) References Cited

U.S. PATENT DOCUMENTS

| | | | |
|---|---|---|---|
| 4,464,175 A | 8/1984 | Altman et al. | |
| 4,776,347 A | 10/1988 | Matthews | |
| 4,981,470 A | 1/1991 | Bombeck, IV | |
| 5,021,043 A * | 6/1991 | Becker | A61F 2/04 128/898 |
| 5,030,227 A | 7/1991 | Rosenbluth et al. | |
| 5,109,869 A | 5/1992 | Buckley | |
| 5,114,401 A | 5/1992 | Stuart et al. | |
| 5,163,927 A | 11/1992 | Woker et al. | |
| 5,209,730 A | 5/1993 | Sullivan | |
| 5,324,269 A | 6/1994 | Miraki | |
| 5,437,290 A * | 8/1995 | Bolger | A61B 5/1076 128/898 |
| 5,591,128 A | 1/1997 | Sithole | |
| 5,657,764 A | 8/1997 | Coulter et al. | |
| 5,709,661 A | 1/1998 | Van et al. | |
| 5,836,895 A | 11/1998 | Ramsey, III | |
| 5,851,210 A | 12/1998 | Torossian | |
| 5,860,923 A | 1/1999 | Lenker et al. | |
| 5,864,961 A | 2/1999 | Vaughan | |
| 6,074,367 A * | 6/2000 | Hubbell | A61M 25/00 206/364 |
| 6,078,832 A | 6/2000 | Lenker et al. | |
| 6,210,338 B1 | 4/2001 | Afremov et al. | |
| 6,241,678 B1 | 6/2001 | Afremov et al. | |
| 6,273,895 B1 | 8/2001 | Pinchuk et al. | |
| 6,494,848 B1 | 12/2002 | Sommercorn et al. | |
| 6,575,932 B1 | 6/2003 | O'Brien et al. | |
| 6,620,114 B2 * | 9/2003 | Vrba | A61M 25/09 33/511 |
| 6,645,233 B1 * | 11/2003 | Ayers | A61F 7/123 607/105 |
| 6,884,257 B1 | 4/2005 | Cox | |
| 7,011,654 B2 * | 3/2006 | Dubrul | A61F 2/958 604/104 |
| 7,022,103 B2 | 4/2006 | Cappiello et al. | |
| 7,048,698 B2 | 5/2006 | Whalen et al. | |
| 7,211,110 B2 | 5/2007 | Rowe et al. | |
| 7,520,876 B2 | 4/2009 | Ressemann et al. | |
| 7,549,997 B2 | 6/2009 | Davis, Jr. et al. | |
| 7,828,793 B2 | 11/2010 | Thompson et al. | |
| 7,837,677 B2 | 11/2010 | Thompson et al. | |
| 7,867,271 B2 * | 1/2011 | Geiser | A61F 2/95 623/1.12 |
| 8,043,285 B2 | 10/2011 | Thompson et al. | |
| 8,080,031 B2 | 12/2011 | Isham | |
| 8,083,692 B2 | 12/2011 | Mangiardi et al. | |
| 8,114,113 B2 | 2/2012 | Becker | |
| 8,512,389 B2 * | 8/2013 | Ayala | A61B 1/018 604/103.04 |
| 8,556,851 B2 | 10/2013 | Hirszowicz et al. | |
| 9,084,558 B2 * | 7/2015 | Furbush, Jr. | A61B 5/065 |
| 9,205,213 B2 * | 12/2015 | Mythen | A61M 16/0472 |
| 9,232,914 B2 * | 1/2016 | Notter | A61B 5/1405 |
| 2002/0029994 A1 | 3/2002 | Schon | |
| 2003/0083594 A1 | 5/2003 | Sommercorn et al. | |
| 2004/0068190 A1 | 4/2004 | Cespedes | |
| 2004/0253185 A1 | 12/2004 | Herweck et al. | |
| 2005/0209674 A1 * | 9/2005 | Kutscher | A61B 17/22 623/1.11 |
| 2006/0015039 A1 * | 1/2006 | Cassidy | A61M 25/09 600/585 |
| 2006/0030864 A1 | 2/2006 | Kennedy et al. | |
| 2006/0052766 A1 * | 3/2006 | Patel | A61M 25/00 604/523 |
| 2006/0116658 A1 | 6/2006 | McMichael et al. | |
| 2007/0060879 A1 * | 3/2007 | Weitzner | A61B 17/12045 604/95.04 |
| 2007/0073269 A1 * | 3/2007 | Becker | A61M 3/0295 604/509 |
| 2007/0106213 A1 | 5/2007 | Spera et al. | |
| 2008/0045896 A1 | 2/2008 | Yribarren et al. | |
| 2008/0188803 A1 | 8/2008 | Jang | |
| 2008/0255475 A1 * | 10/2008 | Kondrosky | A61M 25/09 600/585 |
| 2008/0269643 A1 | 10/2008 | Morriss | |
| 2009/0054760 A1 * | 2/2009 | Burke | A61M 25/0108 600/424 |
| 2009/0131785 A1 | 5/2009 | Lee et al. | |
| 2011/0004057 A1 * | 1/2011 | Goldfarb | A61B 1/233 600/106 |
| 2011/0060275 A1 * | 3/2011 | Christiansen | A61M 25/10 604/101.02 |
| 2011/0098684 A1 * | 4/2011 | Trubiano | A61M 25/04 604/544 |
| 2013/0281971 A1 | 10/2013 | Looper | |
| 2014/0007956 A1 | 1/2014 | Rutty et al. | |
| 2014/0058251 A1 | 2/2014 | Stigall et al. | |
| 2015/0032118 A1 * | 1/2015 | Okamura | A61M 25/0043 606/108 |
| 2015/0045649 A1 * | 2/2015 | O'Dea | A61B 5/6853 600/409 |
| 2015/0099935 A1 * | 4/2015 | Runnels | A61M 16/0488 600/188 |
| 2016/0045218 A1 * | 2/2016 | Swisher | A61B 1/0005 600/104 |

FOREIGN PATENT DOCUMENTS

| | | |
|---|---|---|
| CN | 201840763 U | 5/2011 |
| EP | 1601406 B1 | 9/2004 |
| GB | 2355797 A | 5/2001 |
| JP | 2007020885 A | 2/2007 |
| WO | 2008007350 A1 | 1/2008 |
| WO | 2008033929 A2 | 3/2008 |
| WO | 2008091652 A2 | 7/2008 |
| WO | WO2012037507 A1 | 3/2012 |
| WO | WO2013132070 A2 | 9/2013 |
| WO | WO2013132071 A1 | 9/2013 |
| WO | WO2013134688 A2 | 9/2013 |
| WO | WO2013134691 A1 | 9/2013 |
| WO | WO2013134695 A1 | 9/2013 |
| WO | WO2013134697 A1 | 9/2013 |
| WO | WO2013134701 A2 | 9/2013 |
| WO | WO2013134702 A1 | 9/2013 |
| WO | WO2013134704 A1 | 9/2013 |
| WO | WO2014018659 A2 | 9/2013 |

OTHER PUBLICATIONS dictionary.com defintion of angioplasty, dated Oct. 28, 2016.*
Clinical Research Studies From the Society for Vascular Surgery Journal of Vascular Surgery pp. 886-894e1 Apr. 2011.
Controlling Radiation Exposure in Interventional Cardiology Editor's Perspective J. Dawn Abbott, MD Circ Cardiovasc Interv Aug. 2014.
Clinical Research Studies; From the Society for Vascular Surgery; Journal of Vascular Surgery pp. 886-894e1; Apr. 2011; Comparison of indirect radiation dose estimates with directly measured radiation dose for patients and operators during complex endovascular procedures; Giuseppe Panuccio, MD, Roy K. Greenberg, MD, Kevin Wunderle, MSc, Tara M. Mastracci, MD, Matthew G. Eagleton, MD, and William Davros, PhD; Cleveland, Ohio.

(56) References Cited

OTHER PUBLICATIONS

Radiation exposure to operating room personnel and patients during endovascular procedures; Abhisekh Mohapatra, BA, Roy K. Greenberg, MD, Tara M. Mastracci, MD, Matthew J. Eagleton, MD, and Brett Thornsberry, RT(R) Cleveland, Ohio; Journal of Vascular Surgery Sep. 2013, vol. 58, No. 3; pp. 702-709.

Patient radiation exposure during percutaneous endovascular revascularization of the lower extremity Einat Segal, MD, Ido Weinberg, MD, MSc, Isaac Leichter, PhD, Alexander Klimov, MD, Jay Gin, MD, MPH, and Allan I. Bloom, MD; Jerusalem, Israel; Boston, Mass; and Philadelphia, Pa; Journal of Vascular Surgery; vol. 58, No. 6; Dec. 2013; pp. 1556-1562.

Controlling Radiation Exposure in Interventional Cardiology; Editor's Perspective; J. Dawn Abbott, MD Circ Cardiovasc Interv Aug. 2014 pp. 426-428.

From the Southern Association for Vascular Surgery; Radiation-induced skin injury after complex endovascular procedures; Melissa L. Kirkwood, MD, Gary M. Arbique, PhD, Jeffrey B. Guild, PhD, Carlos Timaran, MD, R. James Valentine, MD and Jon A. Anderson, PhD, Dallas, Tex Journal of Vascular Surgery; vol. 60, No. 3; pp. 742-748; Sep. 2014.

Mini-Focus Issue:Radiation Dose Reduction; Clinical Research; Radiation Dose Reduction in the Cardiac Catheterization Laboratory Utilizing a Novel Protocol; Anthony W. A. Wassef, MD, et al.; Winnipeg, Manitoba, Canada; JACC: Cardiovascular Interventions; vol. 7, No. 5, 2014 © 2 0 1 4 by The American College of Cardiology Foundation ISSN 1936-8798 Published by Elsevier Inc. http://dx.doi.org/10.1016/j.jcin.2013.11.022.

\* cited by examiner

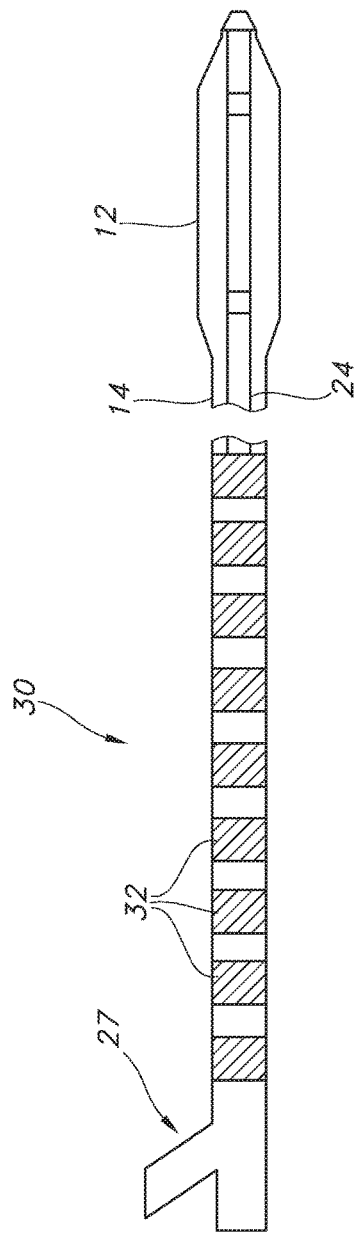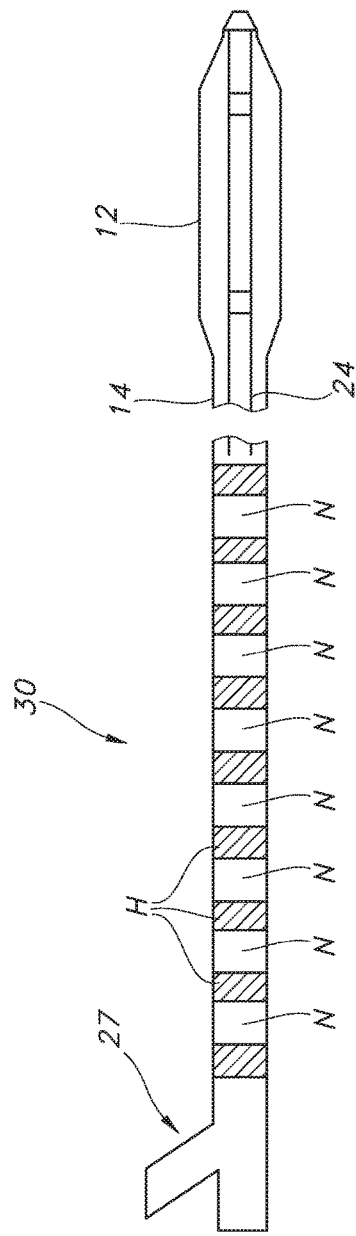

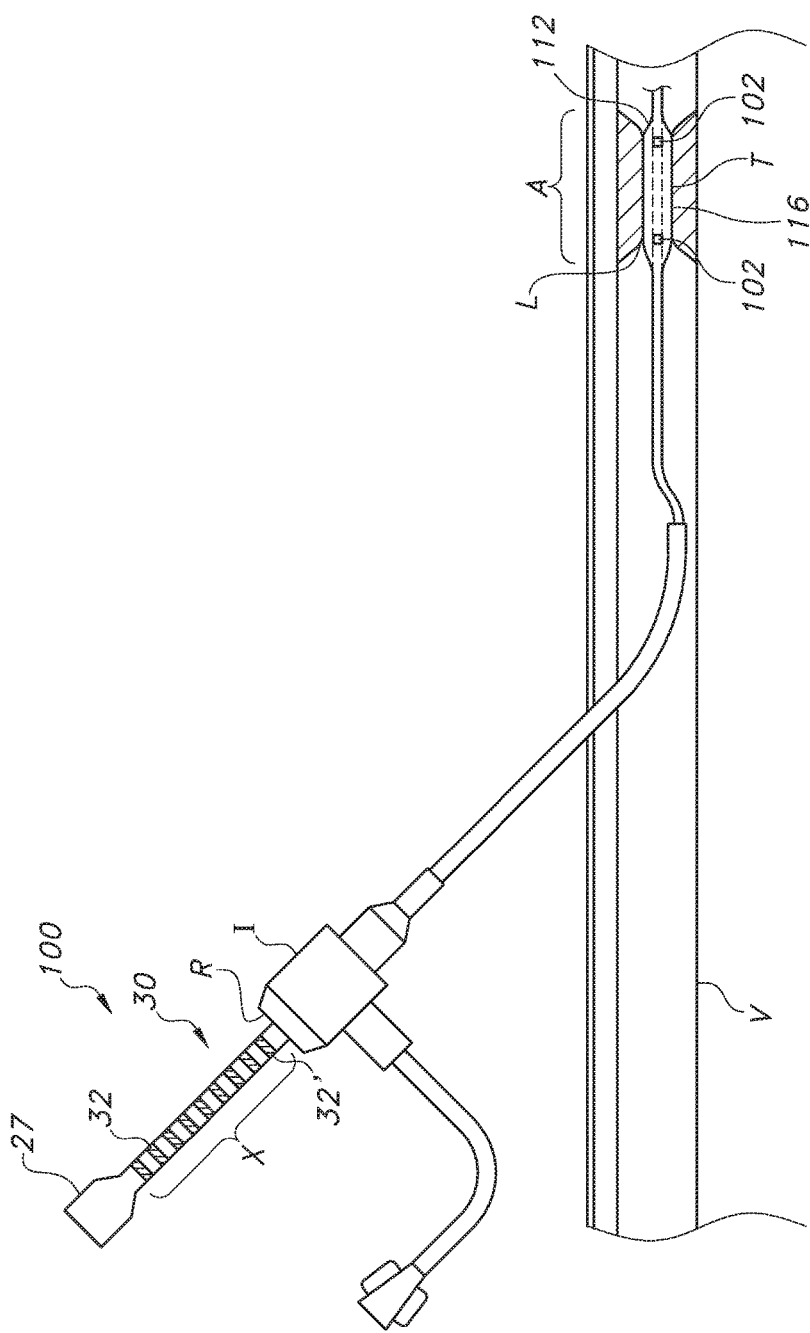

CATHETER WITH MARKINGS TO FACILITATE ALIGNMENT

This application claims the benefit of U.S. Provisional Patent Application Ser. No. 61/747,416, which is incorporated herein by reference.

TECHNICAL FIELD

This disclosure relates generally to interventional medical procedures, such as angioplasty, and, more particularly, to a catheter with markings to assist in ensuring the proper alignment with a treatment area.

BACKGROUND OF THE INVENTION

Catheters including balloons are routinely used to resolve or address flow restrictions or perhaps even complete blockages in tubular areas of a body, such as arteries or veins. In many clinical situations, the restrictions are caused by hard solids, such as calcified plaque, and may sometimes involve the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

The clinician performing the angioplasty procedure should be able to locate the position of the uninflated balloon with accuracy, so that the balloon will be properly positioned once inflated. This is conventionally accomplished by attaching marker bands on the catheter shaft corresponding to the ends of the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

However, misalignment of the marker bands during placement along the shaft sometimes results in their failure to correspond precisely to the extent of the working surface. This misalignment may prevent the clinician from accurately identifying the location of the working surface of the balloon during an interventional procedure. Also, when successive intravascular interventions are made, such as during a pre-dilatation using a first catheter followed by dilatation using a second catheter, the clinician must guess where the pre-dilatation occurred. In either case, this uncertainty may lead to a geographic misalignment, or "miss," of the intended contact between the intended treatment area and the working surface of the balloon. It is especially desirable to avoid such an outcome when the balloon is designed to deliver a payload (such as a therapeutic agent (e.g., a drug, such as paclitaxel, rapamycin, heparin and the like), a drug, a stent, a stent graft, or a combination) or a working element (such as a cutter, focused force wire, or the like) to a specified location within the vasculature, since a miss may, at a minimum, prolong the procedure (such as, for example, by requiring redeployment of the balloon or the use of another balloon catheter in the case of a drug coated balloon), and possibly result in an inferior outcome if the lesion is not properly treated as a result of the misalignment.

Accordingly, a need exists for a manner in which to position a balloon catheter into the vasculature at a treatment area with enhanced accuracy, and also in a manner that is highly repeatable.

SUMMARY OF THE INVENTION

An object of the disclosure is to provide a first catheter with a marking along a proximal portion (e.g., proximal of the distal portion including any balloon) for use in determining at a location external to the body the position relative to a treatment area. A second catheter with a corresponding marking may also be provided for then providing the treatment at the same treatment area.

One aspect of this disclosure pertains to kit for treating a treatment area in the vasculature, comprising a first, pre-dilatation catheter having a first shaft including a first distal portion adapted for positioning at the treatment area and a first proximal portion including a first marking at a first location, and a second, dilatation catheter having a second shaft including a second distal portion adapted for positioning at the treatment area and a second proximal portion including a second marking at a second location substantially matching a first location of the first marking.

The first and second markings may comprise regularly spaced marks or irregularly spaced marks. The first and second markings may be positioned adjacent a hub of the first and second catheters. The markings may be chemiluminescent or photoluminescent.

At least one of the first or second markings may comprise at least one color mark. At least one of the first or second markings comprises at least two marks having different shades.

Each of the first and second catheters may include a balloon. The first distal portion may include one or more radiopaque markings. The second catheter may include a treatment selected from the group consisting of a drug, a stent, a sent graft, a cutter, a focused force wire, or any combination thereof. One or more of the markings may be radiopaque. One or more of the markings may comprise a notch, bump, ridge, recess, or any combination of the foregoing.

Another aspect of the disclosure relates to an apparatus for treating a treatment area at an intravascular location in a body. The apparatus comprises a catheter including a shaft having a distal portion including a balloon carrying a drug and a proximal portion including at least one marking arranged for being viewed at a reference point external to the body for identifying the location of the treatment area relative to the reference point.

The balloon may further include a treatment selected from the group consisting of a stent, a graft, a cutter, a focused force wire, or any combination thereof. The first and second markings may comprise equidistantly spaced bands, and may extend from a first location adjacent a hub of the catheter to a second location closer to the balloon. The markings may be chemiluminescent or photoluminescent, and may comprise at least one color mark. The marking may comprise at least two marks of different shades, and may further include a radiopaque marking. One or more of the markings may comprise a notch, bump, ridge, recess, or any combination of the foregoing.

A further aspect of the disclosure may relate to a method of treating a treatment area in a body. The method comprises inserting a distal portion of a first catheter to the treatment area, determining a position of a first marking on a proximal portion of the first catheter relative to a reference point, and inserting a second catheter until a second marking on the second catheter corresponds to the reference point. The method may further include the step of applying a treatment to the treatment area using the second catheter, and may further include providing the first and second markings in the same color. The determining step may include viewing the first marking at a location external to the body.

A further aspect of the disclosure relates to a method for treating a treatment area in the vasculature. The method comprises providing a first catheter having a first shaft including a first distal portion adapted for positioning at the treatment area and a first proximal portion including a first marking at a first location, and providing a second catheter having a second shaft including a second distal portion adapted for positioning at the first location and a second proximal portion including a second marking at a second location substantially matching a first location of the first marking.

BRIEF DESCRIPTION OF THE DRAWINGS

FIGS. 5 and 6 show details of a catheter according to an embodiment of the present disclosure.

FIGS. 7A, 7B and 8 show a way of using a catheter according to an embodiment of the present disclosure.

MODES FOR CARRYING OUT THE INVENTION

The description provided below and in regard to the figures applies to all embodiments unless noted otherwise, and features common to each embodiment are similarly shown and numbered.

Figure 1:
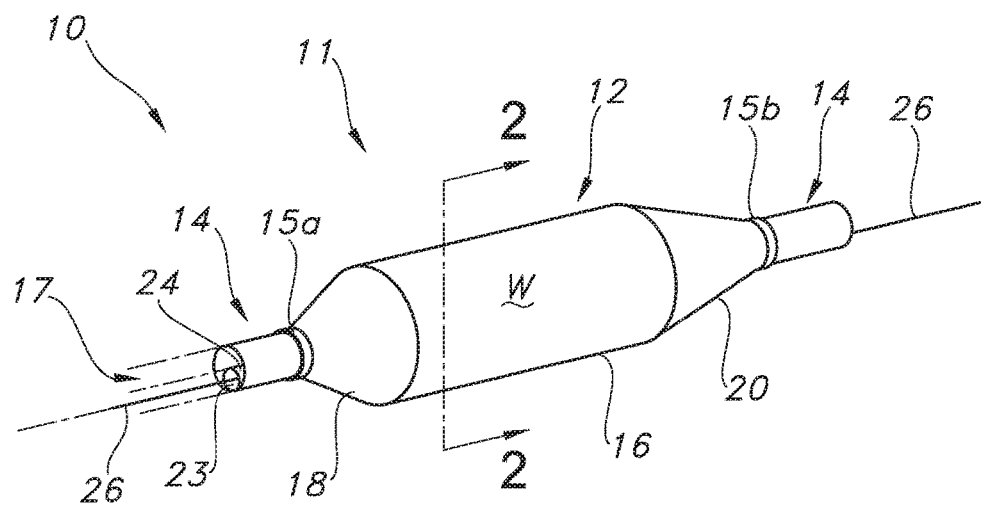
FIGS. 1-4 show a catheter according to an embodiment of the present disclosure.
Figure 2:
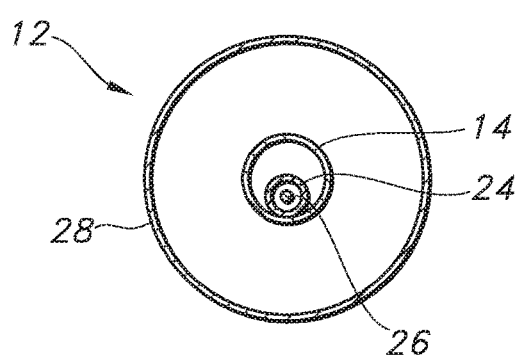
Figure 3:
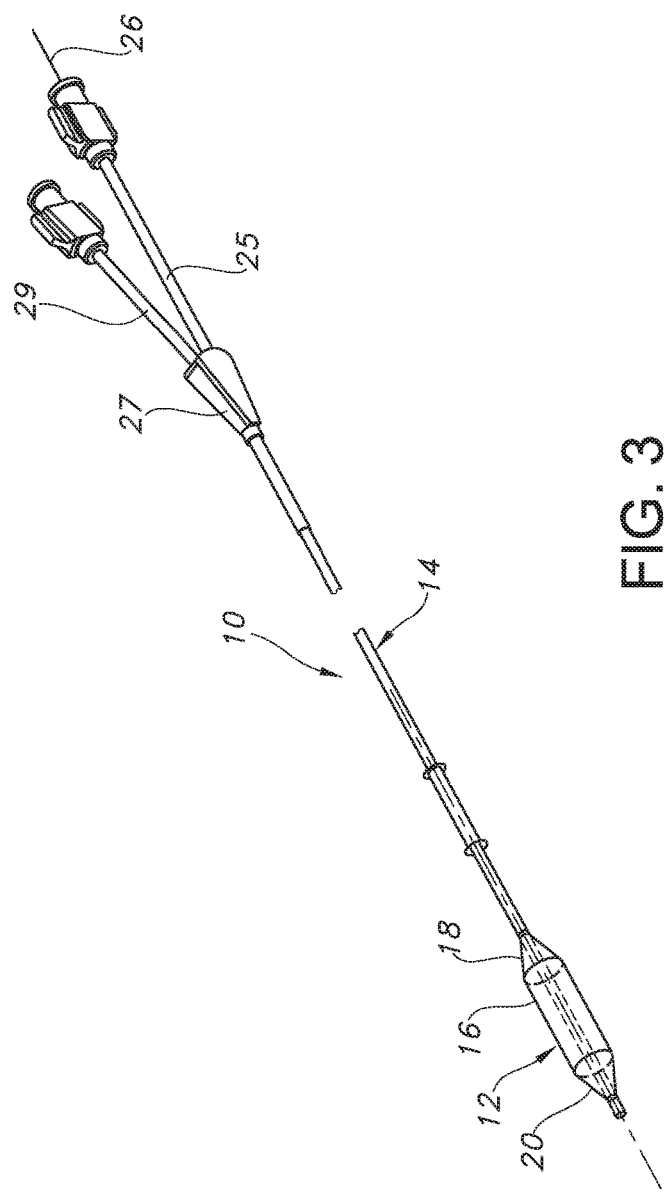

Provided is a catheter 10 having a distal portion 11 with a balloon 12 mounted on a catheter tube 14. Referring to FIGS. 1, 2, and 3, the balloon 12 has an intermediate section 16, or "barrel" having the working surface W, and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12.

Figure 4:
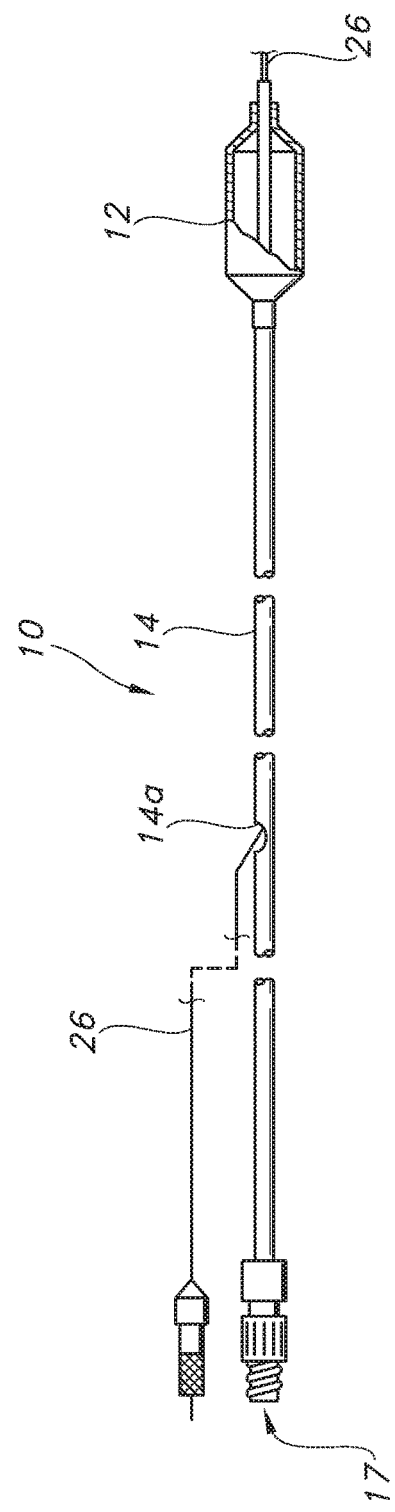

The catheter tube 14 also includes an elongated, tubular shaft 24 forming a guidewire lumen 23 that directs the guidewire 26 through the catheter 10. As illustrated in FIG. 3, this guidewire 26 may be inserted through a first port 25 of a connector, such as a hub 27, into the lumen 23 to achieve an "over the wire" (OTW) arrangement, but could also be provided in a "rapid exchange" configuration in which the guidewire 26 enters the lumen through a lateral opening 14a closer to the distal end (see FIG. 4). A second port 29 may also be associated with catheter 10, such as by way of connector 27, for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use.

Figure 6:
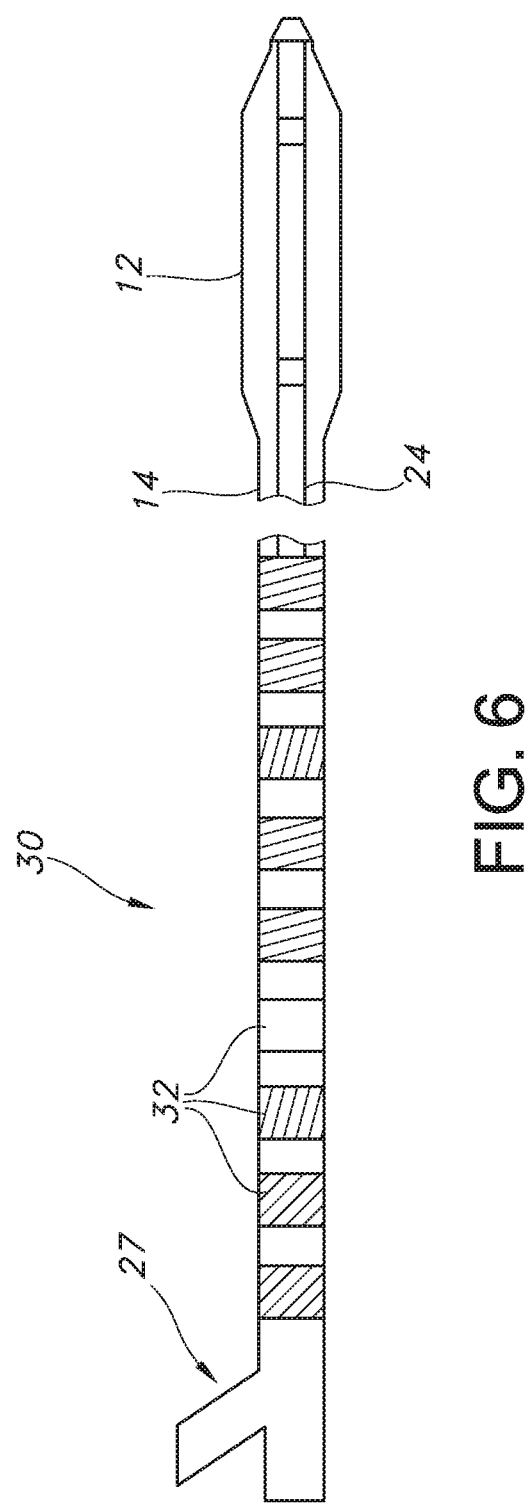

In order to provide an enhanced locatability during an interventional procedure, the catheter 10 may be provided with a marking 30 along a portion external to the body during the procedure, such as along tube 14. As shown in FIG. 5, the marking 30 may comprise a plurality of spaced mark 32, such as bands. These marks 32 may extend from adjacent the connector 27 to the proximal end 15a of the balloon 12, or any portion thereof (which is considered the "proximal portion" of the catheter 10, as contrasted with the distal portion including the balloon 12). The marks 32 may be evenly or unevenly spaced (e.g., the marks may get progressively closer along the length of the shaft 24). The marks 32 may be of a single color, such as for example black as shown in FIG. 5, but as shown in FIG. 6 may also be provided in different shades or colors. The marks 32 may also comprise hash lines H forming a ruler with gradations identified by numbers N (see FIG. 5A), letters, or symbols. The marking 30 may also comprise a biocompatible chemiluminescent or photoluminescent material that may be easily viewed in the low light conditions often present during a procedure involving fluoroscopy. Alternatively or additionally, the marking 30 may be provided in a manner that allows for tactile engagement, such as in the forms of notches, bumps, ridges, recesses, or like structures that can be counted even when not directly visible.

Figure 7B:
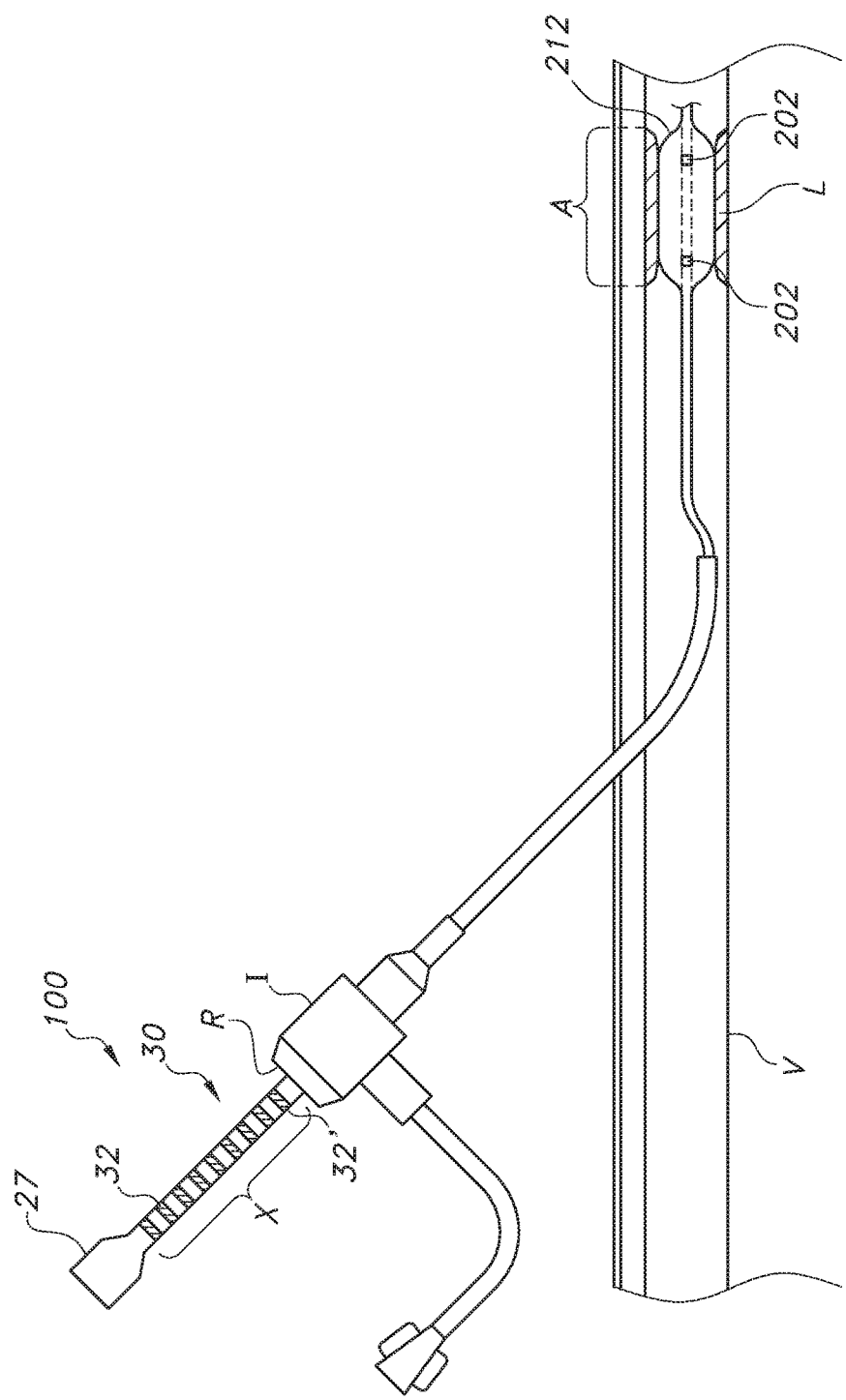

In use, and with reference to FIGS. 7A and 7B, a catheter 100 including the marking 30 may be inserted in to a vessel V to a particular treatment area A, which is shown as comprising a lesion L, but only to provide a pre-dilatation assessment of its location. The catheter 100 may have a radiopaque quality (such as by providing one or more bands 102 underlying the associated balloon 112 and defining the ends of the barrel section 116, or else provided on the balloon surface) that may be used in connection with fluoroscopy to determine the location of the treatment area A. The skilled reader will understand from FIGS. 7A and 7B that this means that the position of the bands 102, or equivalently any sort of radiopaque marker, corresponds to the location of the treatment area A. At this point, the clinician may view the marking 30 to assess the amount to which the catheter 100 has been introduced to the treatment area A. This may involve counting the marks 32 external to the introducer I (for the FIG. 5 embodiment), or else noting a particular color or shade of a particular mark 32' (for the FIG. 6 embodiment), relative to a point of reference R, such as the proximal edge of the introducer I representing a particular distance (X in the illustrated embodiment, which is the distance from the connector 27 to the reference point R).

A second catheter or treatment catheter 200 including a similar marking 30 is then used for providing a treatment T (such as a drug, a stent, a stent graft, a balloon 212 or a combination) to the treatment area A. This catheter 200 may be passed through the introducer I until the corresponding mark 32' aligns with the previously determined point of reference R, which may also correspond to distance X in the event the catheters 100, 200 are of similar lengths). The skilled reader understands from this description that by such a method of positioning, the working surface of the balloon and the treatment area A coincide substantially. The above assures the clinician that the treatment is applied to the treatment area A in the intended manner, and helps to avoid the problem of geographic misalignment. The treatment may then be provided, such as by inflating the balloon 212 of the second catheter 200 to compact the lesion L, and/or deploying the stent or stent graft. Radiopaque markers, such as bands 202, may optionally be provided to aid in confirming the location of the balloon 212 of the second catheter 200.

It is clear to the skilled person from the above passage, when read together with FIGS. 7A and 7B, that for those two catheters, and in fact any kit for treating a treatment area in a patient's vasculature, the locations of the two markings "match". To the skilled person, this can mean that the same or a corresponding marking on both catheters corresponds to the same length from the distal tip of the respective catheter. Put differently, for the same or a corresponding marking on both catheters, the length over which the catheter has been introduced into a patient's vasculature is at least approximately the same.

Figure 8:
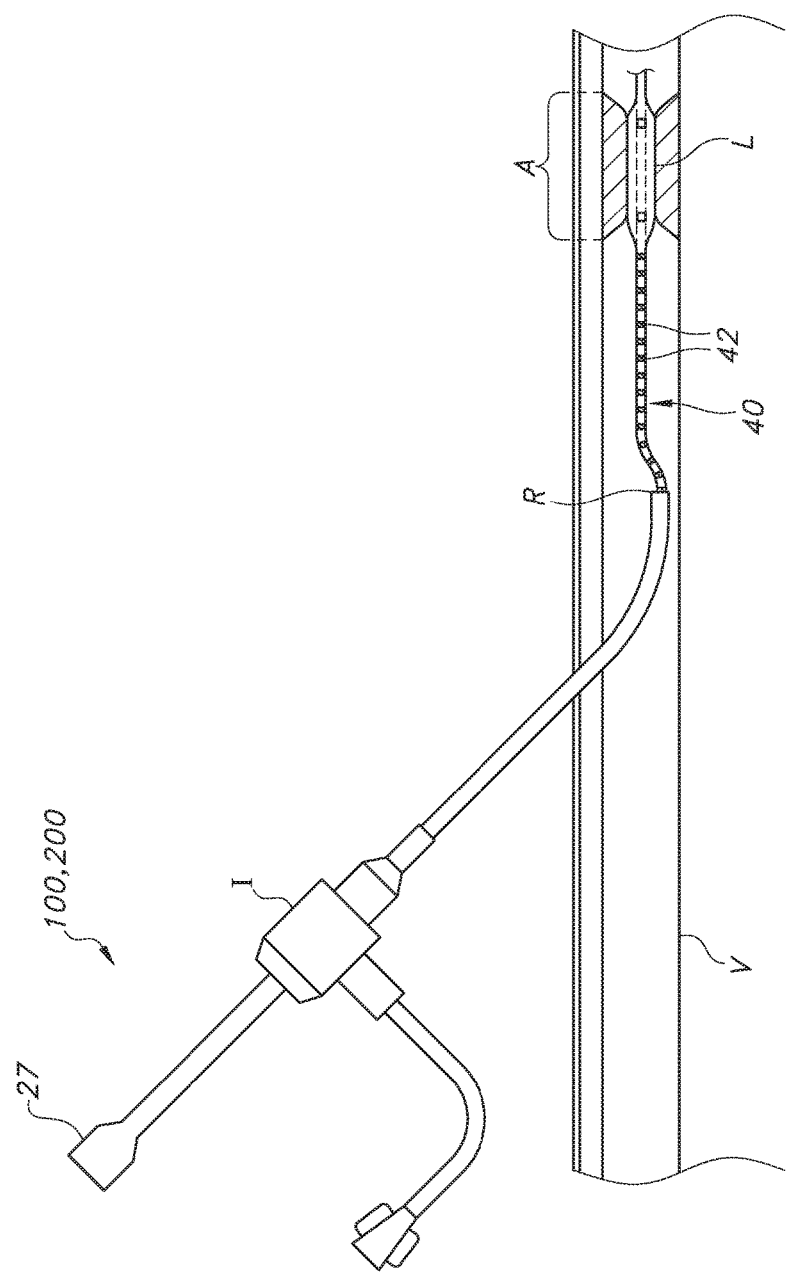

In an alternate approach, the marks may be provided as one or more radiopaque markings 40 formed by spaced marks 42 on the shafts of the catheters 100, 200, instead of or in addition to markings 30. As shown in FIG. 8, a similar counting operation may be done under fluoroscopy during sequential procedures (e.g., interventions), such as by using a different reference point R in the vessel V (including possibly part of the introducer I, such as the outlet or the distal end, which may be made radiopaque as well).

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. A kit for treating a treatment area in a vasculature, comprising:
   a first, pre-dilatation catheter having a first shaft including a first distal portion adapted for positioning at the treatment area and a first proximal portion including a first numerical marking at a first location, the first numerical marking identifying a distance to the treatment area in connection with a reference point external to the vasculature; and
   a second, dilatation catheter having a second shaft including a second distal portion adapted for positioning at the treatment area and a second proximal portion including a second numerical marking at a second location substantially matching the first location of the first marking, the second dilatation catheter including a balloon carrying a drug, the second numerical marking identifying the same distance to the treatment area in connection with the reference point to ensure the drug carried by the balloon is applied to the treatment area, wherein the first and second numerical marking on each catheter indicates a measure of the same length from the respective marking to a distal tip of the respective catheter.

2. The kit of claim 1, wherein the first and second markings are positioned adjacent a hub of the first and second catheters.

3. The kit of claim 1, wherein the first and second markings are chemiluminescent or photoluminescent.

4. The kit of claim 1, wherein the first catheter includes a balloon.

5. The kit of claim 1, wherein the first distal portion includes one or more radiopaque markings.

6. The kit of claim 1, wherein the second catheter includes a treatment selected from the group consisting of a stent, a stent graft, a cutter, a focused force wire, or any combination thereof.

7. The kit of claim 1, wherein one of the first or second markings is radiopaque.

8. The kit of claim 1, wherein each catheter comprises a plurality of numerical markings, the numerical markings on each catheter forming a ruler.

9. A method of treating a treatment area in a body, comprising:
   inserting a distal portion of a first catheter to the treatment area;
   determining a position of the distal portion of the first catheter relative to a reference point by viewing a first numerical marking on the first catheter; and
   inserting a second catheter including a balloon carrying a drug to the treatment area until a second numerical marking on the second catheter corresponds to the reference point, wherein the first and second numerical marking on each catheter indicates a measure of the same length from the respective marking to a distal tip of the respective catheter.

10. The method of claim 9, wherein the determining step comprises counting the number of marks on the first catheter external to an introducer, and the inserting step comprises inserting the second catheter until the same number of marks on the second catheter are external to the introducer.

* * * * *